United States Patent [19]
Henrick et al.

[11] 3,969,384
[45] July 13, 1976

[54] ESTERS OF CYCLOPROPANE ALKANOIC ACIDS

[75] Inventors: Clive A. Henrick; Gerardus B. Staal, both of Palo Alto, Calif.

[73] Assignee: Zoecon Corporation, Palo Alto, Calif.

[22] Filed: June 11, 1975

[21] Appl. No.: 585,986

Related U.S. Application Data

[62] Division of Ser. No. 489,205, July 17, 1974, Pat. No. 3,925,461.

[52] U.S. Cl. .................. 260/410.9 N; 260/410.5; 424/305
[51] Int. Cl.² ........................................ C07C 69/74
[58] Field of Search ................ 260/410.9 N, 410.5, 260/410.6; 424/305

[56] References Cited

UNITED STATES PATENTS

| | | | |
|---|---|---|---|
| 3,671,558 | 6/1972 | Siddall et al. | 260/410.9 N |
| 3,925,460 | 12/1975 | Henrick et al. | 260/468 H |
| 3,925,461 | 12/1975 | Henrick et al. | 260/410.9 N |

*Primary Examiner*—Helen M. McCarthy
*Attorney, Agent, or Firm*—Donald W. Erickson

[57] ABSTRACT

Esters of cyclopropyl substituted carboxylic acids, syntheses thereof, compositions thereof, and use for the control of mites and ticks.

8 Claims, No Drawings

ESTERS OF CYCLOPROPANE ALKANOIC ACIDS

This is a division of application Ser. No. 489,205, filed July 17, 1974 now U.S. Pat. No. 3,925,461.

This invention relates to novel compounds, synthesis thereof, compositions thereof, and the control of mites.

The compounds of the present invention are effective for the control of mites and especially spider mites. Spider mites are plant feeders and cause serious damage to orchard trees, field crops, greenhouse plants and other vegetation. They feed on the foliage and fruit of plants and trees and attack of variety of plants due to their wide distribution. Spider mites of the family Tetanychidae, such as *Tetranychus urticae, Tetranychus canadensis, Tetranychus cinnabarinus, Tetranychus pacificus, Bryobia practiosa, Oligonychus pratensis, Oligonychus ilicis, Panonychus citri, Panonychus ulmi,* and similar related species, are of particular biological interest and economic importance. Other mites are those of the family Tarsonemidae, such as *Steneotarsonemus pallidus*.

Compounds of the present invention of the following formulas I and II are effective control agents for mites.

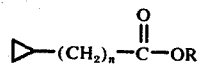  (I)

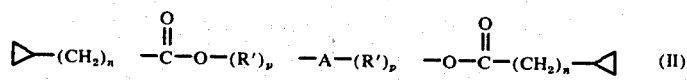  (II)

wherein, n is an even integer between 6 and 14;
n' is an even integer between 6 and 10;
R is alkenyl of two to twenty carbon atoms, alkynyl of two to twenty carbon atoms, phenyl, cycloalkyl optionally substituted by one or more lower alkyl groups, or the group

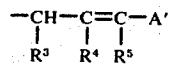

in which each of $R^3$, $R^4$ and $R^5$ is hydrogen or lower alkyl and A' is phenyl, naphthyl, or cycloalkyl, each optionally substituted by one or more halogen, alkyl, alkoxy, aryl, aralkyl, aryloxy or aralkoxy groups;

R' is alkylene of one to six carbon atoms or alkenylene of two to six carbon atoms;
p' is zero or one; and
A is alkylene, alkenylene, alkynylene, cycloakylene of four to six carbon atoms, optionally substituted by one or two alkyl or alkoxy groups; or arylene, optionally substituted by one or two groups selected from alkyl, halogen, or nitro, with the proviso that each compound of Formula I contains at least eighteen carbon atoms in the molecule.

Hereinafter each of n, n', p', R, R', $R^3$, $R^4$, $R^5$, A and A' is as defined above unless otherwise specified.

The compounds of formulas I and II are applied to the mite during the egg, larval or nymphal stages in view of their effect in causing inhibition of egg hatching, abnormal development leading to death, inability to pass from one stage to the next, or inability to reproduce. Some of the compounds also exhibit a residual ovicidal effect. A compound of formula I or II can be applied at concentration levels of the order of 0.001% to 1%, usually 0.01% to 0.1% by weight. Suitable carrier substances include or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound in the formulation is used depending on the type of application apparatus. The formulations can include emulsifying agents and wetting agents to assist in the application and effectiveness of the active ingredient.

The esters of formulas I and II can be prepared by reacting the appropriate alcohol ROH (R is not hydrogen) or dialcohol HO-(R')$_p$' -A-(R')$_p$' -OH with at least one or two moles, respectively of an acid of the formula

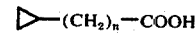

in the presence of an acid catalyst and with heating. The reaction can be carried out in the absence o a solvent; however, use of a solvent inert to the reaction, such as an ether, dichloromethane, chloroform or a hydrocarbon solvent, is preferred. Water may be removed by azeotropic distillation, if desired.

Alternatively, the appropriate acid halide

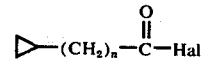

may be reacted with the alcohol KOH (R is not hydrogen) or dialcohol HO-(R')$_p$ -A-(R')$_p$ -OH in the presence of pyridine and at either room temperature or, when the alcohol is sensitive, at from about −10° to about 0°C.

The acids of the formula

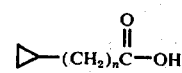

can be prepared by conventional methods known in the art. In one method, cyclopropyl bromide is treated first with lithium and then with copperiodide to form the intermediate

This intermediate is reacted with a halide-substituted ester of the formula

to yield

which is then hydrolyzed to the free acid. In another method, an unsaturated ester of the formula

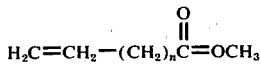

is reacted with methylene iodide in the presence of zinc-copper couple to yield

which is then hydrolyzed to the free acid. Alternatively, the method of U.S. Pat. No. 3,578,685 using cyclopropanecarboxylic acid chloride and 1-morpholinocyclohexene as starting materials is employed.

The preparation of certain acids and alcohols used as starting materials for the compounds of formulas I and II is shown in copending Ser. No. 461,189, filed Apr. 12, 1974 now U.S. Pat. No. 3,925,460, the disclosure of which is hereby incorporated by reference.

The term "alkyl," as used herein, refers to a straight or branched chain saturated aliphatic hydrocarbon group of one to twenty carbon atoms, e.g., methyl, ethyl, propyl, i-propyl, n-butyl, s-butyl, t-butyl, pentyl, hexyl, heptyl, n-octyl, 2-methyloctyl, nonyl, decyl, undecyl, 2-methylundecyl, 6-methylundecyl, dodecyl, pentadecyl and the like. The term "lower alkyl" refers to an alkyl group of one to six carbon atoms.

The term "alkenyl," as used herein, refers to a straight or branched chain unsaturated carbon chain containing two to twenty carbon atoms and having one to three sites of olefinic unsaturation.

The term "alkynyl," as used herein, refers to a straight or branched chain unsaturated carbon chain containing from two to twenty carbon atoms and having one or two sites of acetylenic unsaturation.

The term "cycloalkyl," as used herein, refers to a monovalent cycloalkyl moiety of four to eight carbon atoms, i.e. cyclobutyl, cyclopentyl, cyclohexyl, cycloheptyl, and cyclooctyl.

The term "halogen," as used herein, refers to iodine, chlorine and bromine.

The term "alkoxy," as used herein, refers to a straight or branched chain saturated aliphatic hydrocarbonoxy group of one to fifteen carbon atoms, e.g., methoxy, ethoxy, n-propoxy, i-propoxy, n-butoxy, i-butoxy, n-heptyloxy, n-dodecycloxy, 2-methylotyloxy, and the like.

The term "aryl," as used herein, refers to a monovalent aromatic hydrocarbon group containing from six to fourteen carbon atoms such as phenyl, tolyl, xylyl, mesityl, naphthyl, ethylphenyl, t-butylphenyl, and isopropylphenyl.

The term "aralkyl," as used herein, refers to a monovalent hydrocarbon group containing from seven to fifteen carbon atoms in which a hydrogen atom of an alkyl group having a chain length of one to six carbon atoms is substituted by an aryl group, such as benzyl, phenethyl, methylbenzyl, napthylmethyl and naphthylethyl.

The term "aryloxy," as used herein, refers to an oxy-substituted aromatic hydrocarbon group of six to fourteen carbon atoms, such as phenoxy, naphthyloxy, 4-ethylphenoxy, and the like.

The term "aralkoxyl," as used herein, refers to an aromatic alkyloxy group of seven to fifteen carbon atoms, such as benzyloxy, 2-phenylethoxy, 4-methylbenzyloxy, naphthalenemethoxy, naphthyleethoxy, and the like.

The term "alkylene," as used herein, refers to a bivalent radical derived from a normal or branched chain alkane containing one to ten carbon atoms by removal of a hydrogen atom from each of two carbon atoms or two hydrogen atoms from one carbon atom.

The term "alkenylene" refers to a bivalent radical derived from a normal or branched chain alkene of two to ten carbon atoms by removal of a hydrogen atom from each of two carbon atoms or two hydrogen atoms from one carbon atom.

The term "alkynylene" refers to the bivalent alkynylene moiety including branched chain alkynylene, of two to ten carbon atoms.

The term "cycloalkylene," as used herein, refers to the bivalent cycloalkyl moiety of four to six carbon atoms, i.e. cyclobutylene, cyclopentylene and cyclohexylene.

The term "arylene" refers to any hydrocarbon group of six to twenty carbon atoms and containing at least one aromatic ring, e.g., phenylene or naphthylene, two phenyl or naphthyl rings joined by a single direct bond or by an atom of oxygen, sulfur, or nitrogen, indenylene, fluorenylene, dihydronaphthylene, tetrahydrophthylene, anthracylene, phenathrylene, and the like. The arylene group can be substituted by one or two groups selected from alkyl, halogen, or nitro.

The esters of the present invention can be used alone or in an inert carrier substance for the control of mites (Acarina) or can be used in mixture with pesticides and/or juvenile hormone analogs known in the art in order to obtain a broader spectrum of activity. Suitable insecticides include Baygon, Captin, Sevin, Ciodrin, Systox, Dizinon, Vapona, Galecron, Cygon, Dimethrin, Dursban, Malathion, and Parathion. Typical juvenile hormone analogs which can be used in mixture with the compound of the present invention are described in United States patents 3,752,843 and 3,755,411.

The esters of the present invention are useful for the control of mites and ticks which are ectoparasitic on animals and birds. The compounds can be applied in either solution or in powder (dust) form in a conventional manner. The following examples are provided to illustrate the synthesis of the esters of the present invention and the practice of the present invention. Temperature is in degrees Centigrade. All boiling points were measured by short path distillation.

For those compounds of formula I and II, e.g., the cyclohexane derivatives, where geometrical isomers can exist, each isomer and a mixture of isomers is included unless the isomeric configuration is specifically designated.

EXAMPLE 1

A. A mixture of 12.7 ml. methylene diiodide and 12.2 g. zinc-copper couple in 75 ml. ether is heated under nitrogen for several hours and then 10.0 g. methyl 10-undecenoate in 10 ml. ether is added dropwise. The reaction mixture is refluxed for seven hours, stirred overnight at room temperature, refluxed for eight hours, stirred for five days at room temperature and then refluxed for eight hours.

Excess zinc reagents are decomposed by the dropwise addition of saturated aqueous ammonium chloride solution until a black precipitate is formed. The mixture is filtered through celite and the solid material is washed with ether. The combined ethereal phases are washed, in turn, with 2N sulfuric acid (3 × 50 ml.), 10% aqueous sodium carbonate (4 × 100 ml.), water (2 × 50 ml.) and saturated aqueous sodium chloride (1 × 50 ml.). The ethereal phase is then dried over calcium sulfate, filtered through activity III neutral alumina, concentrated by evaporation, and distilled to yield 7.44 g. of methyl 9-cyclopropylnonanoate, boiling point 107° at 1.0 mm. The product is purified by spinning band distillation.

B. A mixture of 1.20 g. of methyl 9-cyclopropylnonanoate and 0.30 g. of sodium hydroxide in 12 ml. of a 2:1 mixture of methanol and water is stirred at room temperature for four hours. The mixture is acidified with 2N sulfuric acid to a pH of 1 and then extracted with ether (3 × 100 ml.). The combined ethereal phases are washed with water (1 × 50 ml.) and saturated aqueous sodium chloride (2 × 50 ml.) dried over calcium sulfate and the solvent removed to give 0.85 g. of 9-cyclopropylnonanoic acid.

C. A mixture of 0.85 g. of 9-cyclopropylnonanoic acid, 0.45 ml. of thionyl chloride (density 1.656) and 0.10 ml. of dimethylformamide (density 0.945) in 10 ml. ether is stirred overnight at room temperature. The upper layer of the reaction mixture is then separated and the solvent removed by evaporation to yield 9-cyclopropylnonanoyl chloride to which is added at 0° under nitrogen 1.4 g. of 9-octadecen-1-ol and 40 ml. of ether. To this mixture is added dropwise 0.52 ml. of pyridine (density 0.98). The reaction mixture is then stirred ½ hour at 0° and overnight at room temperature. The mixture is filtered, 3 equivalents of water are added and then the mixture is stirred for one hour. Ether is added to dilute the reaction mixture which is washed in turn with 2N sulfuric acid (2 × 50 ml.), 10% aqueous sodium carbonate (2 × 50 ml.), water (2 × 50 ml.) saturated aqueous copper sulfate, water (2 × 50 ml.) and saturated aqueous sodium chloride (1 × 50 ml.). The solution is then dried over calcium sulfate and the solvent removed by evaporation to yield 9-octadecenyl 9-cyclopropylnonanoate which is purified by thin layer chromatography (15% ether/hexane solvent).

EXAMPLE 2

A mixture of 49 g. of 11-bromoundecanoic acid, 500 ml. anhydrous dimethyl formamide, 27.5 g. anhydrous potassium carbonate and 79 g. methyl iodide is heated at 55° for eight hours, then cooled and allowed to sit at room temperature for ten days. The mixture is then filtered and to the filtrate is added ether (250 ml.), pentane (250 ml.) and water (1000 ml.). The organic layer is separated and washed in turn with water (2 × 150 ml.), aqueous saturated sodium chloride (1 × 100 ml.), dried over calcium sulfate and the solvent removed by evaporation to yield 45.56 g. of product which is 27% methyl 11-bromoundecanoate and 53% methyl 11-iodoundecanoate.

Using the procedure of Example 2 with the acids of column I, the esters of column II along with varying amounts of the correspnding iodo esters are prepared.

I 7-chloroheptanoic acid
7-bromoheptanoic acid
9-chlorononanoic acid
9-bromononanoic acid
11-chloroundecanoic acid
13-bromodotridecanoic acid
15-chloropentadecanoic acid

II methyl 7-chloroheptanoate
methyl 7-iodoheptanoate
methyl 7-bromoheptanoate
methyl 9-chlorononanoate
methyl 9-iodononanoate
methyl 9-bromononanate
methyl 11-chloroundecanoate
methyl 11-iodoundecanoate
methyl 13-bromotridecanoate
methyl 13-iodotridecanoate
methyl 15-chloropentadecanoate
methyl 15-iodopentadecanoate

EXAMPLE 3

To a mixture of 2.6 g. of 1% sodium-lithium metal and 120 ml. of anhydrous ether at −15° under argon is slowly added over one hour 27.5 g. of cyclopropyl bromide. The mixture is stirred until the last pieces of lithium disappear and then is kept at −10° ovenight. This mixture is then added, at −20°, to a mixture of 14.4 g. cuprous iodide and 120 ml. tetrahydrofuran. To this mixture is added, dropwise at −20° 15 g. of methyl 11-iodoundecanoate in 5 ml. of tetrahydrofuran. The mixture is then stirred at −20° for 1.5 hours and at 0° for 0.5 hours. Saturated aqueous ammonium chloride solution (100 ml.) is added dropwise with stirring at −20° and then the mixture is concentrated to about ½ volume by evaporation of the solvent. To the concentrated solution is added 200 ml. hexane, the mixture is filtered and the residue is washed with 200 ml. ether. The organic layer is separated and washed in turn with water (2 × 100 ml.), saturated aqueous sodium chloride (1 × 100 ml.) and then dried over calcium sulfate. The solvent is removed by evaporation to yield 10.60 g. methyl 11-cyclopropylundecanoate, b.p. 124° at 0.1 mm.

Using the procedure of Example 3 with the esters of column II, the esters of column III are prepared.

III methyl 7-cyclopropylheptanoate
methyl 9-cyclopropylnonanoate
methyl 11-cyclopropylundecanoate
methyl 13-cyclopropyltridecanoate
methyl 15-cyclopropylpentadecanoate

EXAMPLE 4

A mixture of 5.76 g. methyl 11-cyclopropylundecanoate, 16 ml. methanol, 16 ml. ethanol, 8 ml. water and 1.25 g. sodium hydroxide is boiled for 1.5 hours and then cooled to yield a solid white mass to which is added 200 ml. water and 30 ml. 3N sulfuric acid. The mixture is concentrated by evaporation, 140 ml. ethyl acetate is added and the mixture is stirred overnight. The organic phase is separated and washed in turn with water (2 × 60 ml.) and saturated aqueous sodium chloride, dried over calcium sulfate and the solvent removed to yield 6.10 g. solid 11-cyclopropylundecanoic acid.

Following the procedure of Example 4, the acids of column IV are prepared from the esters of column III.

IV 7-cyclopropylheptanoic acid
9-cyclopropylnonanoic acid
13-cyclopropyltridecanoic acid
15-cyclopropylpentadecanoic acid

EXAMPLE 5

To a mixture of 3.5 g. 11-cyclopropylundecanoic acid, 105 ml. anhydrous ether, and 1.7 ml. thionyl chloride at 24° is added 0.3 ml. of dimethylformamide. The mixture is stirred for 3.5 hours and then the upper layer is separated and the solvent and volatile materials are removed to yield 3.38 g. 11-cyclopropylundecanoyl chloride.

Following the procedure of Example 5, the acid chlorides of column V are prepared from the acids of column IV.

V 7-cyclopropylheptanoyl chloride
9-cyclopropylnonanoyl chloride
13-cyclopropyltridecanoyl chloride
15-cyclopropylpentadecanoyl chloride

EXAMPLE 6

To 60 ml. anhydrous ether and 1.5 g. 7-cyclopropylheptanoyl chloride is added 1.2 g. 2-decyn-1-ol. The mixture is cooled to 0° and 0.8 ml. pyridine is added. The solution is stirred at room temperature for 1 day. The product is worked up using the procedure of Example 1C to yield 2-decynyl 7-cyclopropylheptanoate.

Following the procedure of Example 6, by reacting 7-cyclopropylheptanoyl chloride with each of tetradeca-10,12-dien-1-ol, hexadeca-10,12,14-trien-1-ol, 13,17-dimethyloctadeca-10,12,16-trien-1-ol, octadeca-9,12-dien-1-ol, octadeca-9,11,13-trien-1-ol, 3-decyn-1-ol, octadec-9-yn-1-ol, 7-methyltrideca-5,8-diyn-7-ol, tetradec-2-yn-1-ol, hexadec-4-yn-1-ol and hexadec-9-en-1-ol, the esters of column VI are obtained.

VI tetradeca-10,12-dien-1-yl 7-cyclopropylheptanoate
hexadeca-10,12,14-trien-1-yl 7-cyclopropylheptanoate
13,17-dimethyloctadeca-10,12,16-trien-1-yl 7-cyclopropylheptanoate
octadeca-9,12-dien-1-yl 7-cyclopropylheptanoate
octadeca-9,11,13-trien-1-yl 7-cyclopropylheptanoate
3-decynyl 7-cyclopropylheptanoate
octadec-9-yn-1-yl 7-cyclopropylheptanoate
7-methyltrideca-5,8-diyn-7-yl 7-cycloproplheptanoate
tetradec-2-yn-1-yl 7-cyclopropylheptanoate
hexadec-4-yn-1-yl 7-cyclopropylheptanoate
hexadec-9-enyl 7-cyclopropylheptanoate

EXAMPLE 7

To a solution of 2.5 g. p-methylcinnamyl alcohol in 50 ml. ether at 0° under nitrogen is added 4.9 g. 9-cyclopropylnonanoyl chloride and 3.6 ml. pyridine. The reaction mixture is allowed to warm to room temperature and is then stirred for ten days. Water is then added to dissolve the pyridinium hydrochloride and form a second liquid phase. This mixture is stirred for 4 hours to hydrolyze the excess acid chloride and the mixture is then diluted with a mixture of ether and water. The ether phase is separated and the aqueous phase is extracated once with ether. The combined ether phases are washed with 2N sulfuric acid, 10% potassium carbonate, water, saturated copper sulfate, water, and brine, dried over calcium sulfate and the solvent removed to yield p-methylcinnamyl 9-cyclopropylnonanoate.

Following the procedure of Example 7, the alcohols of column VII are reacted with 9-cyclopropylnonanoyl chloride to yield the esters of column VIII.

VII cinnamyl alcohol
p-methoxycinnamyl alcohol
m-bromocinnamyl alcohol
p-butoxycinnamyl alcohol
p-chlorocinnamyl alcohol
p-ethoxycinnamyl alcohol
3-cyclohexyl-2-propen-1-ol
3-cyclopentyl-2-propen-1-ol
3-cyclobutyl-2-propen-1-ol
3-(4-methoxycyclohexyl)-2-propen-1-ol
3-(4-chlorocyclohexyl)-2-propen-1-ol
3-(1-naphthyl)-2-propen-1-ol
3-(4-chlorophenyl)-3-methyl-2-propen-1-ol
3-(4-methylphenyl)-1-methyl-2-propen-1-ol phenol

VIII cinnamyl 9-cyclopropylnonanoate
p-methoxycinnamyl 9-cyclopropylnonanoate
m-bromocinnamyl 9-cyclopropylnonanoate
p-butoxycinnamyl 9-cyclopropylnonanonate
p-chlorocinnamyl 9-cyclopropylnonanoate
p-ethoxycinnamyl 9-cyclopropylnonanoate
3-cyclohexyl-2-propenyl 9-cyclopropylnonanoate
3-cyclopentyl-2-propenyl 9-cyclopropylnonanoate
3-cyclobutyl-2-propenyl 9cyclopropylnonanoate
3-(4-methoxycyclohexyl)-2-propenyl 9-cycloplynonoate
3-(4-chlorocyclohexyl)-2-propenyl 9-cyclopropylnonanoate
3-(1-naphthyl)-2-propenyl 9-cyclopropylnonanoate 3-(4-chlorophenyl)-3-methyl-2-propenyl 9-cyclopropylnonanonate
3-(4-methylphenyl)-2-methyl-2-propenyl 9-cyclopropylnonanoate phenyl 9-cyclopropylnonanoate

EXAMPLE 8

To a solution of 3.0 g. 1,4-benzenedimethanol in 50 ml. dry ether is added dropwise, under nitrogen, 20.0 g. 7-cyclopropylheptanoyl chloride followed at 0° by pyridine. The reaction mixture is stirred for 3 days under nitrogen, poured into water and extracted with ether. The organic layer is washed with sodium bicarbonate, water and brine, dried over calcium sulfate, and the solvent evaporated to yield 1,4-bis(6-cyclopropylhexylcarbonyloxymethyl)benzene (II, n' = 6, R' = methylene, p' = 1 and A = 1,4-phenylene).

Following the procedure of Example 8, 1,4-benzenedimethanol is reacted with the acid halides of column V where n = 8 and 10 to yield the esters of column IX.

IX 1,4-bis(8-cyclopropyoctylcarbonyloxymethyl)benzene
1,4-bis(10-cyclopropyldecylcarbonyloxymethyl)benzene

EXAMPLE 9

A mixture of 5.5 g. 1,4-dihydroxybenzene, 24 g. 9-cyclopropylnonanoyl chloride, and 2,4 g. magnesium in 55 ml. dry benzene is refluxed for 8 hours. The solution is then diluted with ether, washed with aqueous sodium bicarbonate, dilute aqueous hydrochloric acid, water and brine, dried over calcium sulfate, and recrystallized from ethanol/water to yield 1,4-phenylene bis(9-cyclopropylnonanoate).

Following the procedure of Example 9, 9-cyclopropylnonanoyl chloride is reacted with 2,7-naphthalenediol, 2,5-naphthalenediol, 1,5-naphthalenediol, thiodiphenyl-4,4'-diol, biphenyl-4,4'-diol, and oxydiphenyl-4,4'-diol, 1,4-dihydroxy-2-methylbenzene, 2-chloro-1,4-dihydroxybenzene, 1,4-dihydroxybenzene, 1,4-dihydroxy-2,5-dinitrobenzene, 1,4-dihydroxy-2-ethylbenzene, and 2-bromo-1,4-dihydroxybenzene to yield the respective ester:

2,7-naphthylene bis(9-cyclopropylnonanoate)
2,5-naphthylene bis(9-cyclopropylnonanoate)
1,5-naphthylene bis(9-cyclopropylnonanoate)
4,4'-thiodihenylene bis(9-cyclopropylnonanoate)
4,4'-biphenylene bis(9-cyclopropylnonanoate)
4,4'-oxydiphenylene bis(9-cyclopropylnonanoate),
2-methyl-1,4-phenylene bis(9-cyclopropylnonanoate);
2-chloro-1,4-phenylene bis(9-cyclopropylnonanoate);
2,5-dinitro-1,4-phenylene bis(9-cyclopropylnonanoate);
2-ethyl-1,4-phenylene bis(9-cyclopropylnonanoate);
2-bromo-1,4-phenylene bis(9-cyclopropylnonanoate);

EXAMPLE 10

To a mixture of 3.0 g. of 1,4-butynediol, 150 ml. of dry diethyl ether, and 16.9 ml. of dry pyridine at 0°, under argon is added 25.0 g. 11-cyclopropylundecanoyl chloride over a period of 10 minutes. The mixture is stirred for 2 hours and then water and pentane are added. The mixture is washed with aqueous 3N sulfuric acid, aqueous potassium carbonate, water, aqueous saturated cupric sulfate, water, and brine, dried over calcium sulfate and the solvent removed to yield 1,4-but-2-ynylene bis(11-cyclopropylundecanoate).

Similarly, by reacting 2 molar equivalents of 7-cyclopropylheptanoyl chloride with each of hexa-2,4-dien-1,6-diol, but-1-ene-3,4-diol, 2,5-dimethylhex-3-yne-2,5-diol and hex-3-yne-2,5-diol, the following esters are obtained:

hexa-2,4-dien-1,6-ylene bis(7-cyclopropylheptanoate)
but-1-en-3,4-ylene bis(7-cyclopropylheptanoate)
dimethylhex-3-yn-2,5-ylene bis(7-cyclopropylheptanoate)
hex-3-yn-2,5-ylene bis(7-cyclopropylheptanoate)

EXAMPLE 11

Using the same procedure of Example 10, each of 1,2-ethanediol, 1,3-propanediol, 1,4-butanediol and 1,5-pentanediol, is reacted with 7-cyclopropylheptanoyl chloride to yield the respective bis-ester.

1,2-ethylene bis(7-cyclopropylheptanoate)
1,3-trimethylene bis (7-cyclopropylheptanoate)
1,4-tetramethylene bis(7-cyclopropylheptanoate)
1,5-pentamethylene bis(7-cyclopropylheptanoate)

EXAMPLE 12

To a solution of 10.5 g. 7-cyclopropylheptanoyl chloride in 50 ml. ether at 0° under nitrogen is added 2.0 g. of 1,4-cyclohexanediol, followed by 4.17 ml. of pyridine (specific gravity = 0.98). The reaction mixture is allowed to warm to room temperature and then is stirred for 6 days. A mixture of ether and water is then added, the ether layer is separated, and the aqueous layer is extracted twice with ether. The combined organic phases are washed with 2N sulfuric acid, 10% aqueous sodium carbonate, water, aqueous saturated copper sulfate, water and brine, dried over calcium sulate, the solvent is removed and the residue is recrystallized from hexane to yield 1,4-cyclohexylene bis(-7cyclopropylheptanoate).

Following the above procedure using 9-cyclopropylnonanoyl chloride, 11-cyclopropylundecanoyl chloride as well as 7-cyclopropylheptanoyl chloride as reactants with 1,4-cyclohexanediol and 1,4-cyclohexanedimethanol, the following esters are obtained:

1,4-cyclohexylene bis(9-cyclopropylnonanoate)
1,4-cyclohexylene bis(11-cyclopropylundecanoate)
1,4-dimethylenecyclohexane bis(7-cyclopropylthepanoate)
1,4-dimethylenecyclohexane bis(9-cyclopropylnonanoate)
1,4-dimethylenecylcohexane bis(11-cyclopropylundedanoate)

A wettable powder suitable for field application after dilution can be formulated by blending and then air-milling a mixture of 20 to 30% by an ester of this invention, 60 to 70. % of a solid carrier such as Attaclay X-250, 1 to 3% of an anionic surfactant, such as Igepon T-77, and 3 to 5% of a dispersing agent such as Marasperse N-22.

A typical formulation is as follows:

| | |
|---|---|
| Active ingredient[1] | 25.0% |
| Synthetic calcium silicate | 40.0% |
| Attapulgite Clay | 29.0% |
| Sodium lignosulfonate | 4.0% |

-continued

Sodium N-methyl-N-olcoyl taurate 2.0%

[1]The active ingredient is selected from one or more of the following:
2-decynyl 7-cyclopropylheptanoate
p-methylcinnamyl 9-cyclopropylnonanoate
1,4-phenylene bis(9-cyclopropylnonanoate
1,4-cyclohexylene bis(7-cyclopropylheptanoate)
1,3-trimethylene bis(7-cyclopropylheptanoate)
phenyl 9-cyclopropylnonanoate

What is claimed is:

1. A compound selected from the formula:

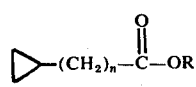

wherein,
n is the integer 6, 8 or 10, and
R is alkenyl of four to sixteen carbon atoms, alkynyl of four to sixteen carbon atoms, phenyl or the group $$-\underset{R^3}{\overset{}{C}}H-\underset{R^4}{\overset{}{C}}=\underset{R^5}{\overset{}{C}}-A'$$

in which each of $R^3$, $R^4$ and $R^5$ is hydrogen, $A'$ is phenyl optionally substituted by chloro, lower alkyl or one to six carbon atoms or alkoxy of one to six carbon atoms, with the proviso that said compound contains at least 18 carbon atoms in the molecule.

2. A compound according to claim 1 wherein the molecule contains less than 27 carbon atoms.

3. The compound, 2-decynyl 7-cyclopropylheptanoate, according to claim 1.

4. The compound, 3-decynyl 7-cyclopropylheptanoate, according to claim 1.

5. The compound, p-methylcinnamyl 9-cyclopropylnonoate, according to claim 1.

6. The compound, phenyl 9-cyclopropylnonanoate, according to claim 1.

7. The compound, p-methoxycinnamyl 9-cyclopropylnonanoate, according to claim 1.

8. The compound, p-chlorocinnamyl 9-cyclopropylnonanoate, according to claim 1.

* * * * *

UNITED STATES PATENT OFFICE
CERTIFICATE OF CORRECTION

Patent No. 3,969,384                    Dated July 13, 1976

Inventor(s)  Clive A. Henrick; Gerardus B. Staal

It is certified that error appears in the above-identified patent and that said Letters Patent are hereby corrected as shown below:

Col. 1, the formula

" $\triangleright\text{-}(CH_2)_n\text{-}\overset{O}{\underset{\|}{C}}\text{-}O\text{-}(R')_p\text{-}A\text{-}(R')_p\text{-}O\text{-}\overset{O}{\underset{\|}{C}}\text{-}(CH_2)_n\text{-}\triangleleft$ " should read -- $\triangleright\text{-}(CH_2)_{n'}\text{-}\overset{O}{\underset{\|}{C}}\text{-}O\text{-}(R')_{p'}\text{-}A\text{-}(R')_{p'}\text{-}O\text{-}\overset{O}{\underset{\|}{C}}\text{-}(CH_2)_{n'}\text{-}\triangleleft$ --.

Col. 2, line 54, the formula "$HO\text{-}(R')_p\text{-}A\text{-}(R')_p\text{-}OH$" should read -- $HO\text{-}(R')_{p'}\text{-}A\text{-}(R')_{p'}\text{-}OH$ --.

Claim 5, line 2, "nonoate" should read --nonanoate--.

Signed and Sealed this

Thirtieth Day of November 1976

[SEAL]

Attest:

RUTH C. MASON
Attesting Officer

C. MARSHALL DANN
Commissioner of Patents and Trademarks